US009097680B1

(12) United States Patent
Fowler

(10) Patent No.: US 9,097,680 B1
(45) Date of Patent: Aug. 4, 2015

(54) APPARATUS AND METHOD FOR DETERMINING SODIUM DIMETHYLDITHIOCARBAMATE IN WATER

(71) Applicant: Randy Fowler, Cleveland, TN (US)

(72) Inventor: Randy Fowler, Cleveland, TN (US)

( * ) Notice: Subject to any disclaimer, the term of this patent is extended or adjusted under 35 U.S.C. 154(b) by 169 days.

(21) Appl. No.: 13/744,555

(22) Filed: Jan. 18, 2013

(51) Int. Cl.
*G01N 33/18* (2006.01)
*G01N 21/79* (2006.01)

(52) U.S. Cl.
CPC ....................................... *G01N 21/79* (2013.01)

(58) Field of Classification Search
USPC .................... 436/106, 119, 163, 166; 422/430
See application file for complete search history.

(56) References Cited

U.S. PATENT DOCUMENTS

| | | | | | |
|---|---|---|---|---|---|
| 3,653,839 | A | * | 4/1972 | Luks et al. ..................... | 436/166 |
| 4,070,281 | A | * | 1/1978 | Tagashira et al. ............. | 210/664 |
| 4,303,610 | A | * | 12/1981 | Sardisco et al. .............. | 422/430 |
| 4,333,908 | A | * | 6/1982 | Maki et al. .................... | 422/430 |
| 4,882,285 | A | * | 11/1989 | Ogleby et al. ................. | 436/98 |
| 5,421,967 | A | * | 6/1995 | Tubergen ...................... | 210/709 |
| 5,470,484 | A | * | 11/1995 | McNeel ......................... | 210/746 |
| 5,856,272 | A | * | 1/1999 | Wilkins, Jr. ................... | 504/151 |
| 2003/0201224 | A1 | * | 10/2003 | Gannon et al. ................ | 210/601 |

OTHER PUBLICATIONS

Stevenson, A. Journal of the Science of Food and Agriculture 1964, 15, 509-522.*
Nitowski, A. J. et al, Journal of Chromatography A 1997, 781, 541-545.*
Malik, A. K. et al, Pesticide Science 1998, 53, 104-106.*
Cao, X. et al, Analytical Methods 2012, 4, 2996-3001.*
Moss, J. "Variable Technologies wins Early Innovator Award" Bussiness Chatt Nov. 13, 2012, 5 pages downloaded from http://businesschatt.com/2012/11/variable-technologies-wins-early-innovator-award/.*

* cited by examiner

*Primary Examiner* — Arlen Soderquist
(74) *Attorney, Agent, or Firm* — Chambliss, Bahner & Stophel, P.C.

(57) ABSTRACT

A water testing system having a water sample container that is adapted to retain the water sample, a color indicator container that is adapted to dispense a color indicator, and a titration reagent container that is adapted to dispense a titration reagent. A method for determining the concentration of sodium dimethyldithiocarbamate in a water sample comprising providing a water testing system having a water sample container that is adapted to retain the water sample, a color indicator container that is adapted to dispense a color indicator, and a titration reagent container that is adapted to dispense a titration reagent. The preferred method also comprises placing the water sample in the water sample container, adding the color indicator to the water sample, adding the titration reagent to the water sample, and determining the concentration of sodium dimethyldithiocarbamate in the water sample.

17 Claims, 3 Drawing Sheets

APPARATUS AND METHOD FOR DETERMINING SODIUM DIMETHYLDITHIOCARBAMATE IN WATER

FIELD OF THE INVENTION

The present invention relates generally to water testing systems, and particularly to water testing systems adapted to determine the concentration of sodium dimethyldithiocarbamate (DTC) in industrial water.

BACKGROUND AND DESCRIPTION OF THE PRIOR ART

It is known to test water to determine the concentration of sodium dimethyldithiocarbamate in the water. Conventional tests, however, suffer from one or more disadvantages. For example, conventional tests require large, heavy, expensive equipment that must be calibrated on a daily basis and materials that are expensive and difficult to purchase. Conventional tests are also complex and require extensive formal training before they can be performed. Further, conventional tests require undesirable delays in receiving the results of the tests.

It would be desirable, therefore, if an apparatus and method for a water testing system could be provided that is compact, light-weight, portable and inexpensive. It would also be desirable if such a water testing system could be provided that uses inexpensive, easily accessible materials and does not require daily calibration. It would be further desirable if such a water testing system could be provided that is simple and does not require extensive formal training, it would be still further desirable if such a water testing system could be provided that produces timely results.

Advantages of the Preferred Embodiments of the Invention

Accordingly, it is an advantage of the preferred embodiments of the invention claimed herein to provide an apparatus and method for a water testing system that is compact, light-weight, portable and inexpensive. It is also an advantage of the preferred embodiments of the invention claimed herein to provide and apparatus and method for a water testing system that uses inexpensive, easily accessible materials and does not require daily calibration. It is another advantage of the preferred embodiments of the invention claimed herein to provide an apparatus and method for a water testing system that is simple and does not require extensive training. It is a further advantage of the preferred embodiment of the invention claimed herein to provide an apparatus and method for a water testing system that produces timely results.

Additional advantages of the preferred embodiments of the invention will become apparent from an examination of the drawings and the ensuing description.
Explanation of the Technical Terms As used herein, the term "water" includes any type of fluid in which sodium dimethyldithiocarbamate may be contained, including without limitation, industrial and municipal wastewater, agricultural irrigation water, ground water, natural bodies of water and the like.

SUMMARY OF THE INVENTION

The apparatus of the invention comprises a water testing system for determining the concentration of sodium dimethyldithiocarbamate in a water sample. The preferred water testing system comprises a water sample container that is adapted to retain the water sample, a color indicator container that is adapted to dispense a color indicator, and a titration reagent container that is adapted to dispense a titration reagent.

The method of the invention comprises a method for determining the concentration of sodium dimethyldithiocarbamate in a water sample. The preferred method comprises providing a water testing system having a water sample container that is adapted to retain the water sample, a color indicator container that is adapted to dispense a color indicator, and a titration reagent container that is adapted to dispense a titration reagent. The preferred method also comprises placing the water sample in the water sample container, adding the color indicator to the water sample, adding the titration reagent to the water sample, and determining the concentration of sodium dimethyldithiocarbamate in the water sample.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 3:
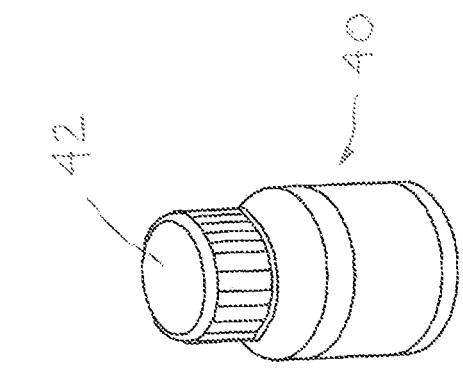
FIG. 3 is a perspective view of the preferred titration reagent container in accordance with the present invention.

Referring now to the drawings, the preferred embodiment of the apparatus and method for a water testing system in accordance with the present invention is illustrated by FIGS. 1 through 6. As shown in FIGS. 1-6, the preferred embodiment of the apparatus and method for a water testing system is adapted to be a compact, light-weight, portable and inexpensive quantitative field analytical water testing system. The preferred embodiment of the apparatus and method for a water testing system is also adapted to use inexpensive, easily accessible materials and does not require daily calibration. The preferred embodiment of the apparatus and method for a water testing system is further adapted to be simple and does not require extensive training. The preferred embodiment of the apparatus and method for a water testing system is still further adapted to produce timely results.

Figure 1:
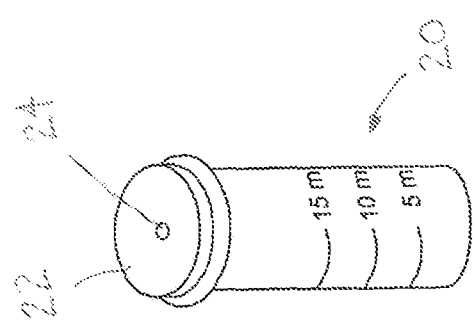
FIG. 1 is a perspective view of the preferred embodiment of the water sample container in accordance with the present invention.

Referring now to FIG. 1, a perspective view of the preferred embodiment of the water sample container of the water testing system in accordance with the present invention is illustrated. As shown in FIG. 1, the preferred water sample container is designated generally by reference numeral 20. The preferred water sample container 20 is adapted to receive, retain and dispense an approximately 15 milliliter (mL) water sample and includes markings such as graduating lines reflecting 5 mL, 10 mL and 15 mL. The preferred water sample container 20 also includes cap 22. Preferred cap 22 is adapted to be removably affixed to the open end of water sample container 20. Preferred cap 22 also includes aperture 24 which is adapted to permit fluid to be added to the water sample retained by water sample container 20. While FIG. 1 illustrates the preferred configuration and arrangement of the water sample container and cap, it is contemplated within the scope of the invention that the water sample container and cap may be of any suitable configuration and arrangement.

Figure 2:
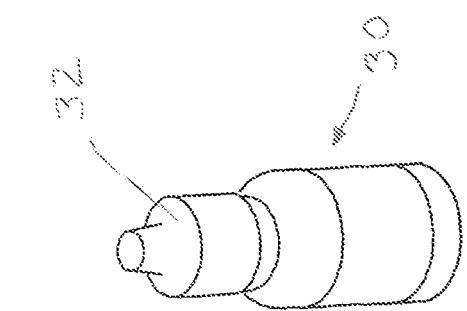
FIG. 2 is a perspective view of the preferred color additive container in accordance with the present invention.

Referring now to FIG. 2, a perspective view of the preferred color additive container of the water testing system in accordance with the present invention is illustrated. As shown in FIG. 2, the preferred color additive container is a drop bottle and designated generally by reference numeral 30. The preferred drop bottle 30 includes bottle cap 32. The preferred drop bottle 30 is adapted to receive, retain and dispense a color indicator. Preferably, drop bottle 30 is adapted to dispense a drop (approximately 0.04545 milliliters) of liquid color indicator at a time. Preferably, a drop of color indicator is added to the 15 mL water sample using drop bottle 30. While FIG. 2 illustrates the preferred configuration and arrangement of the color additive container, it is contemplated within the scope of the invention that the color additive container may be of any suitable arrangement and configuration.

Still referring to FIG. 2, the preferred color indicator is adapted to change the color of a water sample when the water sample includes sodium dimethyldithiocarbamate (DTC). More particularly, the preferred color indicator is adapted to change the color of the water sample from clear to a color ranging from yellow to brown depending upon the concentration of sodium dimethyldithiocarbamate in the water sample. Preferably, the color indicator comprises a 25 w/v % solution of copper sulfate pentahydrate ($CuSO_4.5H_2O$). The molecular weight of the preferred color indicator compound is approximately 249,686 grams. Consequently, a 1 molar (1 M or 25%) solution may be prepared by dissolving 250 grams of copper sulfate pentahydrate in approximately 700 mL of deionized water (DI) in a volumetric flask. The flask is then preferably filled to the one liter mark (1,000 mL) with DI and blended thoroughly for a period of approximately 60 minutes or until completely dissolved. It is contemplated within the scope of the invention that the color additive may be of any suitable composition adapted to change the color of a water sample when the water sample contains DTC.

Referring now to FIG. 3, a perspective view of the preferred titration reagent container of the water testing system in accordance with the present invention is illustrated. As shown in FIG. 3, the preferred titration reagent container is adapted receive, retain and dispense a titration reagent and is designated by reference numeral 40. The preferred titration reagent container 40 includes removable reagent cap 42. The preferred titration reagent is adapted to return the water sample and color indicator mixture to an uncolored or clear condition. More particularly, the preferred titration reagent is slowly added, drop-by-drop, to the water sample and color indicator mixture until the water sample is clear. While FIG. 3 illustrates the preferred configuration and arrangement of the titration reagent container, it is contemplated within the scope of the invention that the titration reagent container may be of any suitable configuration and arrangement and that the water testing system comprises more than one titration reagent container.

Still referring to FIG. 3, the preferred titration reagent comprises an approximately 0.2 w/v % (2 grams per liter) solution of sodium hypochlorite (NaOCl). The molecular weight of this compound is approximately 74.4 grams, or 7.44 w/v % in solution. Sodium hypochlorite is available commercially as 6 w/v % (60 g/L, which is 0.806 Molar), 5.25 w/v % (52.5 g/L, which is 0.706 Molar) and industrially as 15 w/v % (150 g/L, which is 2.02 Molar). Sodium hypochlorite is known as generic bleach, laundry bleach, or Clorox® bleach. Preparing a 2 gram per liter (0.27 Molar) solution may be accomplished by pipetting 33.33 milliliters of 6% bleach into a 1000 mL volumetric flask, then filling to the 1000 mL mark with DI and slowly blending on a magnetic stirring table for a period of 60 minutes. While the foregoing describes the preferred composition and method for producing the titration reagent, it is contemplated within the scope of the invention that the titration reagent may be of any suitable composition for determining the concentration of DTC in a water sample and may be produced by any suitable process.

Preferably, the formulating equation for the titration reagent is as follows: 2 g/L NaOCl/60 g/L NaOCl×1,000 mL total volume=33.33 mL NaOCl. Because the desired concentration of sodium hypochlorite solution is 2 g/L (grams per liter), and sodium hypochlorite is available in a concentration of 60 g/L, it is necessary to divide 2 g/L by 60 g/L. The resulting quotient, 0.03333, is then multiplied by 1,000, which is the total volume (1 liter) that DTC reagent is prepared as. It may be prepared in other volumes, but this is the standard volume. The product, 33.33, represents the number of milliliters of 60 g/L sodium hypochlorite solution that is used to make 1 liter by dilution with DI.

Figures 4, 5:
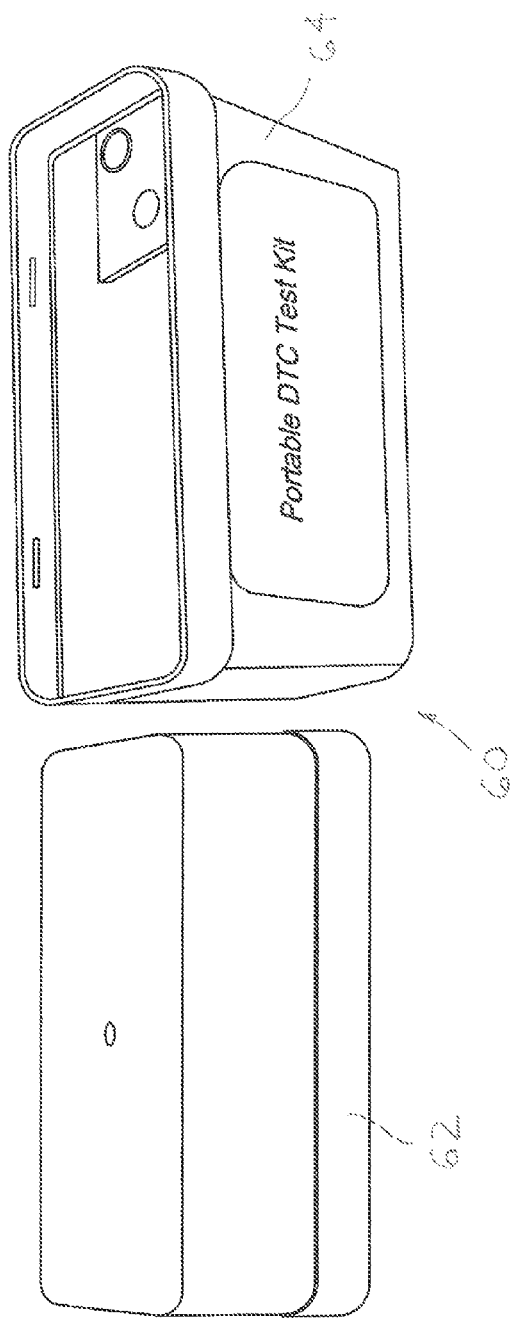
FIG. 4 is a front view of the preferred syringe in accordance with the present invention.
FIG. 5 is a perspective view of the preferred water testing system carrier in accordance with the present invention.

Referring now to FIG. 4, a front view of the preferred titration reagent dispenser of the water testing system in accordance with the present invention is illustrated. The preferred titration reagent dispenser is a syringe and generally designated by reference numeral 50. Preferred syringe 50 includes plunger 52, plunger end 54 and distal end 56. Preferred syringe 50 also comprises graduated numerals ranging from zero (0) to two hundred (200) parts per million and is adapted to hold approximately 1.1 milliliters of titration reagent. Preferred syringe 50 is also adapted to receive, retain and dispense a titration reagent. More particularly, preferred syringe 50 is adapted to add a titration reagent, drop by drop, to a water sample and color indicator mixture. While FIG. 4 illustrates the preferred configuration and arrangement of the titration reagent dispenser, it is contemplated within the scope of the invention that the titration reagent dispenser may be of any suitable arrangement and configuration.

Referring now to FIG. 5, a perspective view of the preferred carrier of the water testing system in accordance with the present invention is illustrated. As shown in FIG. 5, the preferred carrier is designated generally by reference numeral 60. The preferred carrier 60 is adapted to receive water sample container 20, drop bottle 30, titration reagent container 40 and syringe 50. Preferred carrier 60 is adapted to provide a portable water testing system. The preferred carrier 60 includes top portion 62 and bottom portion 64. While FIG. 5 illustrates the preferred configuration and arrangement of the carrier, it is contemplated within the scope of the invention that the carrier may be of any suitable arrangement and configuration.

Figure 6:
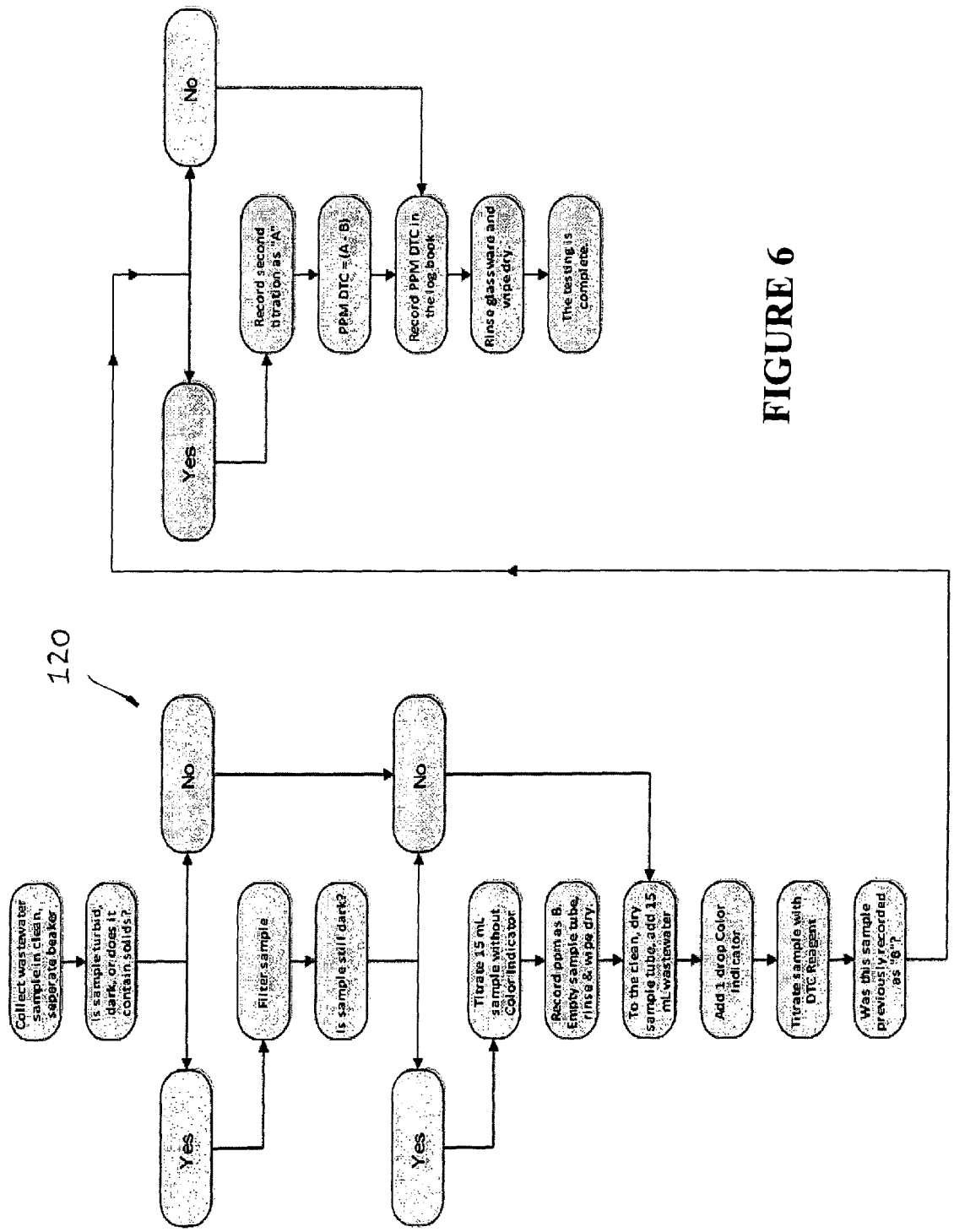
FIG. 6 is a flow chart illustrating the preferred method for determining the concentration of DTC in a water sample in accordance with the present invention.

Referring now to FIG. 6, the invention also comprises a method for determining the concentration of sodium dimethyldithiocarbamate in a water sample. As shown in FIG. 6, the preferred method for determining the concentration of sodium dimethyldithiocarbamate in a water sample is designated generally by reference numeral 120. The preferred method comprises providing a water testing system as described above.

Still referring to FIG. 6, the preferred method also comprises placing a water sample in a water sample container, adding a color indicator to the water sample, adding a titration reagent to the water sample, and determining the concentration of sodium dimethyldithiocarbamate in the water. In the preferred method, a drop or approximately 0.04545 mL, of the color indicator is added to a 15 mL water sample. If the water sample contains sodium dimethyldithiocarbamate, the color indicator solution will change the color of the sample from clear to a color ranging from yellow to brown depending upon the concentration of sodium dimethyldithiocarbamate. If the water sample does not change color after the color indicator solution is added, then the sample does not contain any sodium dimethyldithiocarbamate.

Still referring to FIG. 6, in the preferred method, approximately 1.1 mL of titration reagent is added to the syringe, and the titration reagent is added, drop-by-drop, to the water sample and color indicator mixture until the water sample is clear. The syringe is marked such that the distal end of the plunger coincides with the marking representing zero (0) when the syringe contains 1.1 milliliters of titration reagent. The syringe is marked from zero (0) to two hundred (200) parts per million. By slowly applying a force to the plunger while gently swirling the water sample container, the titration reagent is added one drop at a time to the water sample through the aperture in the cap of the water sample container until the water sample returns to its original color, i.e. clear. When the water sample has returned to clear, the distal end of the plunger coincides with marking representing the concentration of sodium dimethyldithiocarbamate contained in the water sample in parts per million.

Still referring to FIG. 6, if the distal end of the plunger coincides with the marking representing 200 ppm before the water sample returns to clear, then the syringe may be refilled with the titration reagent to the zero (0) marking. A force is then slowly applied to the plunger and the titration reagent is added to the water sample until the water sample is clear. When the water sample is clear, the distal end of the plunger coincides with the marking representing the concentration of sodium dimethyldithiocarbamate plus 200 ppm. If the water sample is not clear after 2.2 milliliters of titration reagent are added to the water sample, then the syringe is refilled and 400 ppm is added to the result achieved in the third round. If the water sample is again not clear after emptying the contents of the syringe, the process can be repeated until the water sample returns to a clear condition.

Still referring to FIG. 6, the preferred method also comprises the step of collecting a water sample of approximately 100 mL in a clean beaker or other suitable container means and determining if the water sample is turbid (cloudy) or dark or if it contains solids such as particulates. If any of these conditions exist, the water sample is preferably filtered into another clean container using a coffee filter and a small funnel. It is contemplated within the scope of the invention, however, that any suitable filtering means could be used to filter a water sample that is dark or cloudy or contain particulates. If none of these conditions exist after the water sample is filtered, then the process described above is followed.

If, however, any of these conditions still exist in the water sample after it has been filtered, titration reagent is added to a 15 mL filtered water sample until none of the conditions exist, i.e. the water sample is clear. The amount of titration reagent added to the 15 mL water sample is recorded in terms of ppm (as measured on the syringe) as value "B." The 15 mL water sample is then removed from the water sample container and a second 15 mL water sample from the same filtered water used in the first measurement is placed into the water sample container, a drop of color indicator is added to the water sample, and titration reagent is added drop by drop until the water sample is clear again. Preferably, the water sample container may be gently swirled as the titration reagent is slowly added to the 15 mL water samples. The amount of titration reagent added to the second filtered water sample is again recorded in terms of ppm (as measured on the syringe) as value "A." Then, value B is subtracted from value A to determine the level of DTC in the water sample in terms of ppm. The DTC level can be recorded in a log book or other suitable medium including without limitation an electronic device.

After cleaning the water sample container and any other beakers or the like used to collect the water sample, the process may be repeated.

If the water sample collected has a DTC concentration in excess of 2,000 ppm, dark brown precipitates may begin to form. According to an alternative embodiment of the method of the invention, a 5 mL water sample is added to 10 mL of distilled or deionized water and mixed. A drop of color indicator may be added to the water sample and titration reagent may thereafter be added, drop-by-drop, until the water sample is clear. The amount of titration reagent added to the water sample and color indicator mixture is determined in ppm as indicated by the syringe and that amount is multiplied by three (3) to obtain the concentration of DTC in the water sample. While FIG. 6 illustrates the preferred sequence of the steps of the method for determining the concentration of sodium dimethyldithiocarbamate in a water sample, it is contemplated within the scope of the invention that the steps of the method of the invention may be performed in any suitable sequence.

If DTC is being added to an industrial wastewater treatment system by an electronic metering pump, the current pump control settings (PCS) when an effluent water sample is pulled may be recorded. When the sample has been analyzed and the DTC concentration (PPM DTC) has been determined, the desired pump control settings may be calculated using the following equation: Desired PCS=Desired PPM DTC/Existing PPM DTC×Current PCS. By way of example, if the pump speed is set at 100 beats per minute (BPM) and the DTC concentration is determined to be 70 ppm, and a DTC concentration of 10 ppm is desired, the calculation is equated as follows: 10 ppm DTC/70 ppm DTC×100 BPM=14.3 BPM. Thus, in this example, the pump speed should be dropped to about 14 beats per minute. It may still be necessary to repeat the analysis several times to establish the correct pump speed for each individual case.

In most cases, operators who run DTC find that a safe residual DTC concentration is approximately 10 ppm. Typically, DTC is prepared and sold as a liquid solution in which the molecular concentration of sodium dimethyldithiocarbamate is 40%. To determine the actual concentration of the DTC molecule within a tested water sample, one may use the following equation: PPM Actual DTC Molecule in the Water Sample=PPM DTC×0.4. After determining the actual DTC molecule concentration, the Milligrams per Liter (mg/L) of DTC can be calculated using the following equation: Mg/l DTC Molecule PPM Actual DTC Molecule in the Water Sample×0.8547. Parts per Million (PPM) and Milligrams per Liter (mg/L) are slightly different because DTC has a density of 1.17 g/mL. Consequently, one may calculate mg/L by multiplying PPM by 0.8547. Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A method for determining the concentration of sodium dimethyldithiocarbamate in a water sample, said method comprising:
   (a) providing a water testing system, said water testing system comprising:
      (1) a water sample container, said water sample container being adapted to retain the water sample;
      (2) a color indicator container, said color indicator container being adapted to dispense copper sulfate;
      (3) a titration reagent container, said titration reagent container being adapted to dispense sodium hypochlorite;
   (b) placing the water sample in the water sample container;
   (c) adding the copper sulfate to the water sample;
   (d) adding the sodium hypochlorite to the water sample; and
   (e) determining the concentration of sodium dimethyldithiocarbamate in the water sample.

2. The method of claim 1 wherein the titration reagent container comprises a syringe.

3. The method of claim 2 wherein the syringe comprises graduated numerals ranging between zero and approximately two hundred ppm.

4. The method of claim 2 wherein approximately 1.0 mL of sodium hypochlorite is added to the syringe.

5. The method of claim 1 wherein the water testing system further comprises a carrier.

6. The method of claim 1 wherein the water testing system is portable.

7. The method of claim 1 wherein the water sample container is adapted to hold approximately 15 mL of water.

8. The method of claim 1 wherein approximately 0.04545 mL of copper sulfate is added to the water sample.

9. The method of claim 1 wherein the sodium hypochlorite is added to the water sample until the water sample is clear.

10. A water testing system for determining the concentration of sodium dimethyldithiocarbamate in a water sample, said water testing system comprising:
   (a) a water sample container, said water sample container being adapted to receive the water sample;
   (b) a color indicator container and copper sulfate, said color indicator container being adapted to dispense the copper sulfate which is adapted change the color of the water sample when the water sample includes sodium dimethyldithiocarbamate;
   (c) a titration reagent container and sodium hypochlorite, said titration reagent container being adapted to dispense the sodium hypochlorite which is adapted change the color of the water sample to clear;
   wherein the sodium hypochlorite is added to the mixture of the water sample and the copper sulfate until the water sample is clear;
   and wherein the concentration of sodium dimethyldithiocarbamate is determined based on the amount of sodium hypochlorite added to the mixture of the water sample and the copper sulfate.

11. The water testing system of claim 10 wherein the titration reagent container comprises a syringe.

12. The water testing system of claim 11 wherein the syringe comprises graduated numerals ranging between zero and approximately two hundred ppm.

13. The water testing system of claim 11 wherein approximately 1.0 mL of sodium hypochlorite is added to the syringe.

14. The water testing system of claim 10 wherein the water testing system further comprises a carrier.

15. The water testing system of claim 10 wherein the water testing system is portable.

16. The water testing system of claim 10 wherein the water sample container is adapted to hold approximately 15 mL of water.

17. The water testing system of claim 10 wherein approximately 0.04545 mL of copper sulfate the is added to the water sample.

* * * * *